US00PP14086P29

(12) United States Plant Patent
Heims

(10) Patent No.: US PP14,086 P2
(45) Date of Patent: Aug. 19, 2003

(54) PULMONARIA PLANT NAMED 'BUBBLE GUM'

(75) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 10/213,893

(22) Filed: Aug. 6, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—Klarquist Sparkman, LLP

(57) ABSTRACT

A new and distinct hybrid of Pulmonaria plant characterized by silvered foliage and rose pink flowers that stay rose pink rather that fading to violet and mildew resistance.

1 Drawing Sheet

Botanical classification: Pulmonaria hybrid.
Variety denomination: 'Bubble Gum'.

The present invention relates to a new and distinct cultivar a hardy perennial of the genus Pulmonaria, and known by the cultivar name 'Bubble Gum'. The genus Pulmonaria is a member of the family Boraginaceae.

The new cultivar originated as an open-pollinated cross between unknown parents in a field of selected hybrid Pulmonaria. This is known to be an outcross because Pulmonaria does not normally self-pollinate. Due to the fact that the instant plant and parent plants are interspecific hybrids from several generations of interbreeding and selecting, no species designations are given.

The new variety has been reproduced only by asexual propagation (division and tissue culture). Each of the progeny exhibits identical characteristics to the original plant.

This plant is characterized by the following:

1. Silvered foliage.
2. Pink flowers that don't change from purple violet to pink to violet.
3. Mildew resistance.

This new cultivar has been reproduced only by asexual propagation (division and tissue culture). Each of the progeny exhibits identical characteristics to the original plant. Asexual propagation by tissue culture using standard micropropagation techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
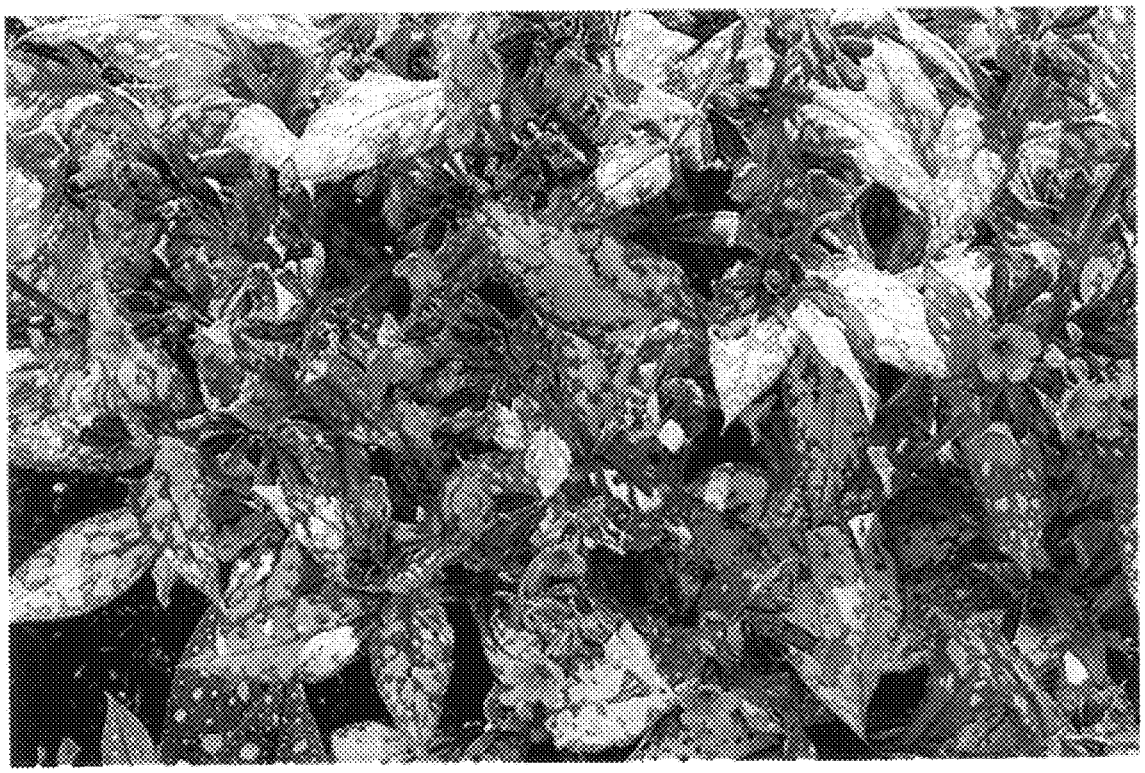
FIG. 1 shows Pulmonaria 'Bubble Gum' in flower in the spring.
Figure 2:
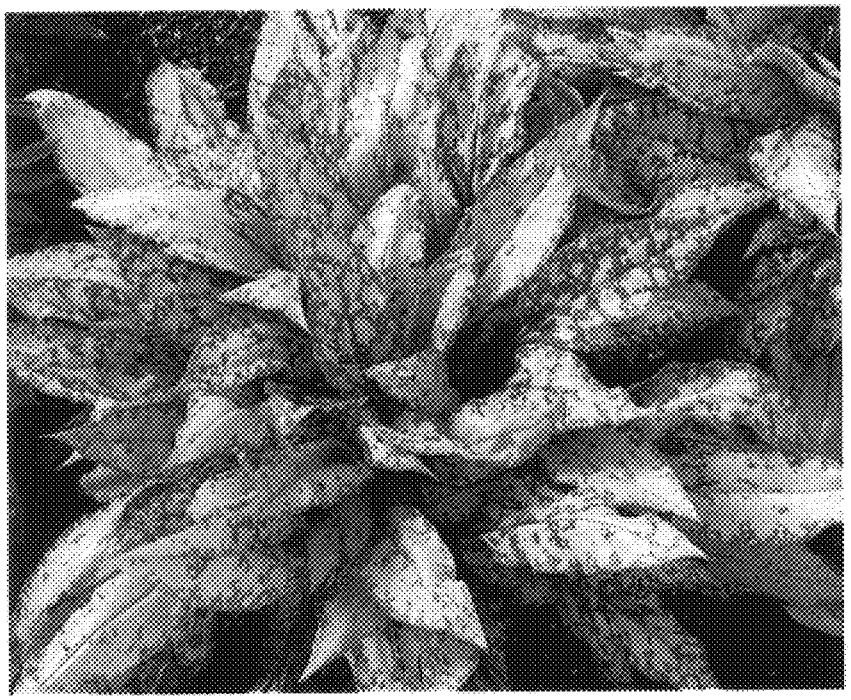
FIG. 2 shows the foliage in the garden in July in Canby, Oreg.

The following is a detailed description of the new Pulmonaria hybrid based on observations of a one-year old specimen grown in the garden in Canby, Oreg. The color descriptions are all based on The Royal Horticultural Society Colour Chart.

Botanical name: Pulmonaria hybrid.
Cultivar name: 'Bubble Gum'.
Plant:
- *Type.*—Herbaceous perennial.
- *Hardiness.*—USDA Zones 5 to 9.
- *Spring size.*—30 cm. wide and 20 cm. tall when first flowering.
- *Summer size.*—53 cm. wide and 3o cm. tall.
- *Form.*—Basal clump.

Leaf:
- *Type.*—Simple.
- *Shape.*—Lanceolate.
- *Arrangement.*—Rosette.
- *Length.*—35 cm. long including petiole.
- *Width.*—7.5 cm. at widest.
- *Petiole length.*—12 cm.
- *Margins.*—Entire, undulating in small waves just along the margin.
- *Apex.*—Acuminate.
- *Base.*—Attenuate.
- *Leaf texture.*—Scabrous.
- *Petiole texture.*—Scabrous.
- *Petiole color.*—Yellow Green 146D except edges Green 137A.
- *Venation.*—Reticulate.
- *Color.*—Topside — Varies from mostly silvered leaves (Greyed Green 193B) with green (Green 137A) edges to green with large silver blotches. Bottom — Yellow Green 146C.

Cauline leaves (found in the spring only on the flowering stems):
- *Type.*—Simple.
- *Arrangement.*—Alternate.
- *Shape.*—Oblanceolate near bottom of the stem and ovate near the top.
- *Length.*—5.4 cm.
- *Width.*—0.9 cm.
- *Margins.*—Undulate.
- *Apex.*—Acuminate.
- *Base.*—Clasping, sessile.
- *Leaf texture.*—Hirsute.

*Venation.*—Pinnate.

*Color.*—Topside: Green 137A with spots or blotches of silvering, Greyed Green 193B. Bottom side: Yellow Green 147C.

Inflorescence:

*Type.*—Terminal forked cyme.

*Peduncle.*—Height: 18 cm. Diameter: 0.4 cm. Color: Closest to Yellow Green 146C. Texture: Scabrous.

*Pedicel.*—Length: Varies. Grows to 1 cm. Texture: Scabrous. Color: Greyed Orange 177A.

Flower bud:

*Size.*—1.6 cm. long and 0.4 cm. wide.

*Shape.*—Ovoid.

*Color.*—Rose red. Red Group 51A to 41A.

Flower:

*Type.*—Actinomorphic.

*Shape.*—Funnelform.

*Size.*—2 cm. deep and 1.5 cm. wide.

*Corolla.*—5 fused petals with rounded lobes.

*Color.*—Rose pink. Red 52B to 47A.

*Calyx.*—5 fused sepals, tubular campanulate, parted ⅓ to base, scabrous. Color — Dark maroon brown. Greyed Orange 177A to Brown 200A. Size — 1.6 cm deep and 0.6 cm wide.

*Pistil.*—1.5 cm., pin type, exerted from corolla tube.

*Ovary position.*—Partly inferior.

*Carpel number.*—4.

*Stamen number.*—5, attached to the tube.

*Pollen color.*—White 155A.

*Bloom period.*—Late February to late April in Canby, Oreg.

*Fragrance.*—None.

Seed:

*Type.*—4 smooth nutlets, Black 202A and shiny, typical of the genus.

*Fertility.*—Fertile.

Disease: Mildew resistant. Mildew is a common problem with Pulmonaria and no damage has been observed on plants of this new cultivar in the garden or when grown under commercial conditions in Canby, Oreg.

COMPARISONS TO SIMILAR PULMONARIA

Compared to Pulmonaria 'Victorian Brooch' (U.S. Plant Pat. No. 11,234), the instant plant has more silvering on the leaves, a rose pink flower color that doesn't fade to violet, and a darker calyx.

Compared to Pulmonaria 'Northern Lights' (U.S. Plant Pat. No. 13,124), the instant plant has rose pink flowers that don't vary from violet to pink to violet, margins that have many shallow undulations along the margin rather than deep undulations, and smaller less silvered leaves.

Compared to Pulmonaria 'Raspberry Splash' (U.S. Plant Pat. No. 12,138), this new cultivar has smaller, rounder leaves, darker calyces, and a round rather than sprawling habit.

I claim:

1. A new and distinct hybrid of Pulmonaria plant substantially as shown and described, characterized by a combination of silvered foliage and rose pink flowers that stay rose pink rather than fading to violet.

* * * * *